(12) United States Patent
Cinbis et al.

(10) Patent No.: US 9,918,638 B2
(45) Date of Patent: Mar. 20, 2018

(54) ULTRALOW-POWER IMPLANTABLE HUB-BASED WIRELESS IMPLANTABLE SENSOR COMMUNICATION

(71) Applicant: Medtronic, Inc., Minneapolis, MN (US)

(72) Inventors: Can Cinbis, Salt Lake City, UT (US); Michael A Schugt, St. Paul, MN (US); Richard J O'Brien, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/296,847

(22) Filed: Oct. 18, 2016

(65) Prior Publication Data

US 2017/0100036 A1    Apr. 13, 2017

Related U.S. Application Data

(63) Continuation of application No. 13/190,737, filed on Jul. 26, 2011, now abandoned.

(51) Int. Cl.
*A61B 5/00*    (2006.01)
*A61N 1/372*    (2006.01)
*A61N 1/37*    (2006.01)

(52) U.S. Cl.
CPC ......... *A61B 5/0031* (2013.01); *A61B 5/0028* (2013.01); *A61N 1/37211* (2013.01); *A61B 2560/0209* (2013.01)

(58) Field of Classification Search
CPC ....... G06K 19/07309; G06K 19/07318; G06K 19/07373; G06K 19/07336; G06K 19/07345; G06K 19/07354; G06K 19/07363; G06K 19/07372; G06K 19/07381; G06K 7/0008; G06K 7/10316; G06K 7/10366; G06K 7/10376; G06K 7/10386; G06K 7/10396; G06K 7/10405; A61B 5/0028; A61B 5/0031; A61B 2560/0209; A61N 1/37211
USPC ......................................................... 340/10.1
See application file for complete search history.

(56) References Cited

U.S. PATENT DOCUMENTS

| | | | |
|---|---|---|---|
| 5,113,859 A | 5/1992 | Funke | |
| 5,534,018 A | 7/1996 | Wahlstrand et al. | |
| 5,814,089 A * | 9/1998 | Stokes | A61N 1/3787 607/32 |
| 6,016,448 A | 1/2000 | Busacker et al. | |
| 6,154,675 A * | 11/2000 | Juran | A61N 1/3708 607/27 |

(Continued)

FOREIGN PATENT DOCUMENTS

| | | | |
|---|---|---|---|
| EP | 1022035 A1 | 7/2000 | |
| WO | 2010126342 A2 | 11/2010 | |
| WO | WO 2010126342 A2 * | 11/2010 | ........... H04L 9/0833 |

OTHER PUBLICATIONS

Prosecution History from U.S. Appl. No. 13/190,737, dated May 28, 2013 through Nov. 7, 2013 55 pgs.

*Primary Examiner* — Omar Casillashernandez (57) ABSTRACT

Communication power in a medical device system is managed by providing power from a power supply to a communication circuit in a sensing device according to a first communication wake up mode set for a first time period and according to a second communication wake up mode set for a second time period. The second communication wake-up mode is established by a second device.

20 Claims, 7 Drawing Sheets

(56) References Cited

U.S. PATENT DOCUMENTS

| | | | |
|---|---|---|---|
| 6,263,246 B1* | 7/2001 | Goedeke | A61N 1/08 607/30 |
| 6,418,346 B1 | 7/2002 | Nelson et al. | |
| 6,442,433 B1 | 8/2002 | Linberg | |
| 6,599,250 B2 | 7/2003 | Webb et al. | |
| 6,622,045 B2 | 9/2003 | Snell et al. | |
| 6,681,135 B1 | 1/2004 | Davis et al. | |
| 6,740,075 B2 | 5/2004 | Lebel et al. | |
| 7,187,979 B2 | 5/2007 | Haubrich et al. | |
| 7,610,099 B2 | 10/2009 | Almendinger et al. | |
| 7,697,994 B2 | 4/2010 | VanDanacker | |
| 7,761,164 B2 | 6/2010 | Verhoef et al. | |
| 7,751,890 B2* | 7/2010 | McCabe | A61N 1/3706 600/510 |
| 7,893,828 B2* | 2/2011 | Kates | G08B 1/08 340/10.1 |
| 3,185,210 A1 | 5/2012 | Haubrich et al. | |
| 8,185,210 B2* | 5/2012 | Haubrich | A61B 5/0006 375/260 |
| 2004/0204744 A1 | 10/2004 | Penner et al. | |
| 2006/0007863 A1 | 1/2006 | Naghian | |
| 2006/0031378 A1 | 2/2006 | Vallapureddy et al. | |
| 2006/0041478 A1 | 2/2006 | Zheng | |
| 2006/0092855 A1 | 5/2006 | Chiu | |
| 2006/0255131 A1* | 11/2006 | Stewart | G06K 7/10039 235/383 |
| 2007/0027495 A1* | 2/2007 | Gerber | A61N 1/36007 607/41 |
| 2007/0299480 A1 | 12/2007 | Hill | |
| 2008/0046037 A1 | 2/2008 | Haubrich et al. | |
| 2008/0046038 A1* | 2/2008 | Hill | A61B 5/0031 607/60 |
| 2008/0071328 A1 | 3/2008 | Haubrich et al. | |
| 2010/0152815 A1* | 6/2010 | Vandanacker | G06F 19/3418 607/60 |
| 2010/0217347 A1* | 8/2010 | Swoyer | A61N 1/3601 607/42 |
| 2013/0027186 A1 | 1/2013 | Cinbis et al. | |

* cited by examiner

ULTRALOW-POWER IMPLANTABLE HUB-BASED WIRELESS IMPLANTABLE SENSOR COMMUNICATION

RELATED APPLICATION

This application is a continuation of U.S. patent application Ser. No. 13/190,737, filed Jul. 26, 2011 entitled "ULTRALOW-POWER IMPLANTABLE HUB-BASED WIRELESS IMPLANTABLE SENSOR COMMUNICATION", which is herein incorporated by reference in its entirety.

TECHNICAL FIELD

The present disclosure relates generally to medical devices and, in particular, to a medical device system and associated method for wireless communication.

BACKGROUND

A wide variety of implantable medical devices (IMDs) are available for monitoring physiological conditions and/or delivering therapies. Such devices may include sensors for monitoring physiological signals for diagnostic purposes, monitoring disease progression, or controlling and optimizing therapy delivery. Examples of implantable monitoring devices include hemodynamic monitors, ECG monitors, and glucose monitors. Examples of therapy delivery devices include devices enabled to deliver electrical stimulation pulses such as cardiac pacemakers, implantable cardioverter defibrillators, neurostimulators, and drug delivery devices, such as insulin pumps, morphine pumps, etc.

IMDs are often coupled to medical leads, extending from a housing enclosing the IMD circuitry. The leads carry sensors and/or electrodes and are used to dispose the sensors/electrodes at a targeted monitoring or therapy delivery site while providing electrical connection between the sensor/electrodes and the IMD circuitry. Leadless IMDs have also been proposed which incorporate electrodes/sensors on or in the housing of the device.

Physical connection of an IMD to sensors implanted deeply in a patient's body or distributed in various body locations to enable communication of sensed signals to the IMD can be cumbersome, highly invasive, or simply not feasible depending on a desired sensor implant location. Furthermore, as sensors become miniaturized to facilitate minimally-invasive surgical methods and implantation at very specific monitoring sites, the power capacity of such sensors becomes limited due to physical size of the sensor. As implantable device technology advances, and the ability to continuously and remotely provide total patient management care expands, there is an apparent need for providing efficient wireless communication of data acquired by implantable physiological sensors.

DETAILED DESCRIPTION

In the following description, references are made to illustrative embodiments. It is understood that other embodiments may be utilized without departing from the scope of the disclosure. For example, while communication power management methods and apparatus described herein are described in various embodiments to be implemented in implantable physiological sensors, the methods described may be implemented in medical devices that are external or wearable.

Figure 1:
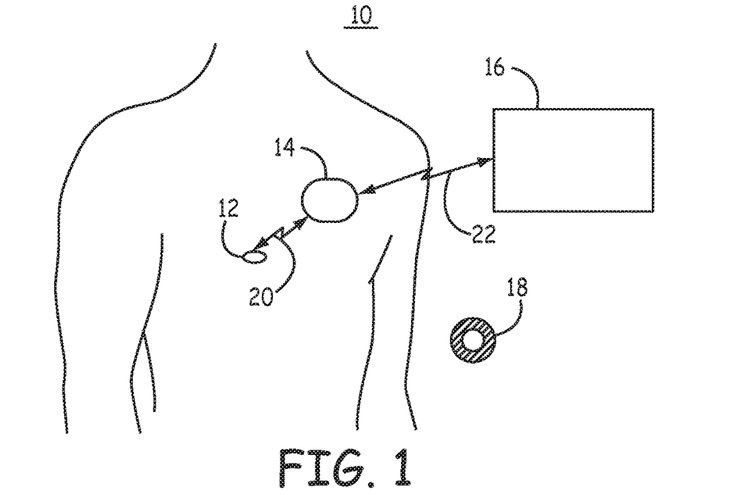
FIG. 1 is a schematic diagram of an implantable medical device system according to one embodiment.

FIG. 1 is a schematic diagram of an implantable medical device system 10 according to one embodiment. System 10 includes a sensing device 12, a communication hub 14, and an external communication device 16. Sensing device 12 is provided for sensing at least one physiological signal. Sensing device 12 is a miniaturized device having a limited power supply available, due to its small size, for powering the primary sensing operation of the device and for other functions such as transmitting and receiving data through wireless communication operations. Sensing device 12 is configured as a wireless device to enable minimally-invasive implantation methods, such as by needle injection, without the associated limitations of tunneling and coupling a medical electrical lead to device 12. Sensing device 12 may be implanted intra- or extravascularly, deeply in the patient's body or at body locations remote from hub 14.

Sensing device 12 may incorporate one or more of numerous types of physiological sensors, including but not limited to, a pressure sensor, oxygen sensor, accelerometer, pH, glucose, or other chemical sensor, temperature sensor, acoustical sensor, electrodes for measuring EEG or EMG signals, impedance signals, or cardiac signals, etc. Sensing device 12 typically does not include therapy delivery capabilities due to its small size and limited power supply, however, communication methods described herein do not exclude embodiments in which the wireless sensing device 12 is capable of delivering some type of therapy to the patient.

Communication hub 14 is provided with relatively greater power capacity available for communication operations than sensing device 12. Communication hub 14 is provided with or without therapy delivery and/or sensing functionality. Communication hub 14 is adapted for extracutaneous, subcutaneous or submuscular implantation, or more generally nearer to the patient's skin than a potentially deeper implant location of sensing device 12. Communication hub 14 may be a dedicated communication device to provide transmission of data from sensing device 12 to an external device 16

(or another implanted device located remotely from sensing device 12). In other embodiments, communication hub 14 may include sensing and/or therapy delivery capabilities. For example, hub 14 may be embodied as a pacemaker, ICD, neurostimulator, ECG monitor, hemodynamic monitor or the like. Hub 14 may be a wireless device as shown, but in other embodiments one or more leads may extend from hub 14 as necessary for other sensing or therapy delivery functions performed by hub 14.

A relatively short-distance, low power communication link 20 provides bidirectional communication between sensing device 12 and hub 14 (as compared to a communication link that would be required if sensing device 12 were communicating directly with external device 16). Communication link 20 may utilize conduction of communication signals through body tissues. Reference is made, for example, to U.S. Pat. No. 5,113,859 (Funke), hereby incorporated herein by reference in its entirety. Hub 14, being larger and/or more superficially implanted than sensor 12 provides relatively higher power communication signals for transmission of data acquired by sensing device 12 over a relatively longer distance to external device 16. In this way, the power supply of sensing device 12 may be miniaturized and conserved for powering the primary sensing operations of device 12. Power needed for transmitting data acquired by device 12 to external device 16 is minimized by the use of communication hub 14.

External device 16 may be a programmer, home monitor, personal computer, a communication device, or other external device configured to receive data from hub 14 via communication link 22. External device 16 is used to program or send commands to sensing device 12 via hub 14. External device 16 may be further coupled to a communication network for transmitting data to a remote patient management database to enable a clinician to remotely review data retrieved from sensing device 12. In some embodiments, hub 14 may communicate directly with a communication device or system. For example, external device 16 may represent a cell phone tower and hub 14 is configured to transmit and receive cellular signals to and from a cell phone via the cell phone tower. Reference is made to commonly-assigned U.S. Pat. Nos. 6,599,250 (Webb et al.), 6,442,433 (Linberg et al.) 6,622,045 (Snell et al.), 6,418,346 (Nelson et al.), and 6,480,745 (Nelson et al.) for general descriptions and examples of network communication systems for use with implantable medical devices for remote patient monitoring and device programming, all of which patents are hereby incorporated herein by reference in their entirety.

As will be described herein, communication circuitry within device 12 is normally powered off, referred to as a "sleep mode", during which the communication circuitry cannot transmit or receive communication signals. Sensing device 12 and/or hub 14 may include a reed switch or other mechanism that can be actuated by an external activator 18, such as a magnet, to manually cause the communication circuitry within sensing device 12 or hub 14 to be powered up to an "awake" state, such that it is enabled to send and/or receive communication signals. This manual activation of the communication circuitry of device 12 and/or hub 14 may be used in an emergency situation, during an implant procedure, during office visits, or other times when communication with sensing device 12 is required.

Figure 2:
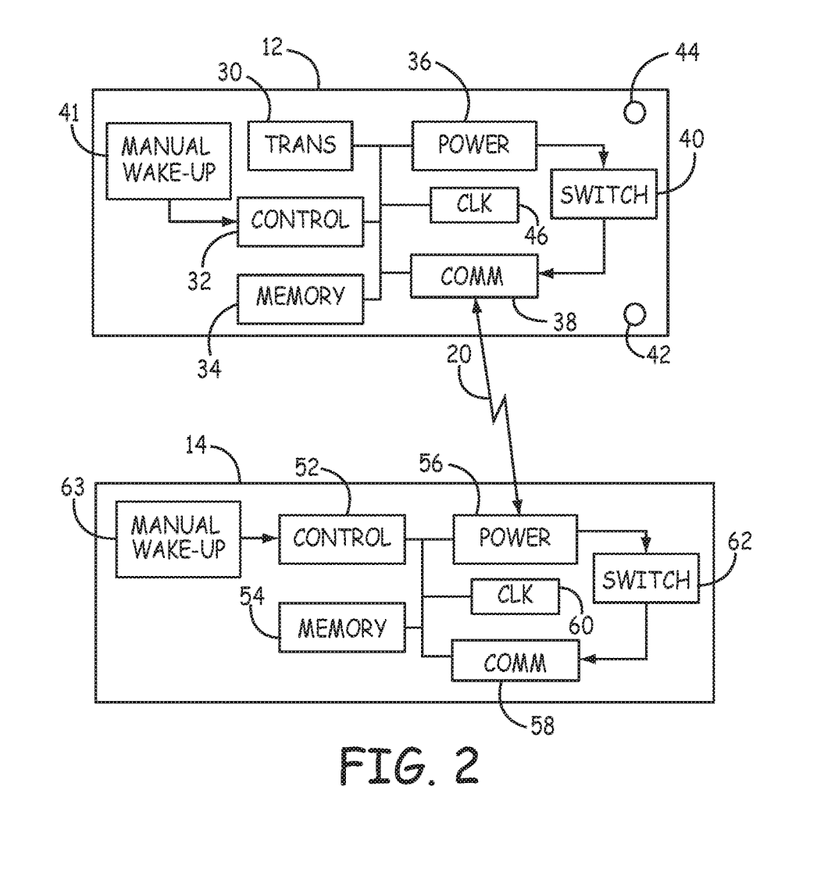
FIG. 2 is a functional block diagram of sensing device and communication hub according to one embodiment.

FIG. 2 is a functional block diagram of sensing device 12 and communication hub 14 according to one embodiment. Sensing device 12 includes at least one transducer 30 and/or sensing electrodes 42 and 44 for monitoring at least one physiological signal, which may be an acoustical, pressure, oxygen, flow or other type of physical signal or an electrical signal such as an EMG or impedance signal. Control processor 32 and associated memory 34 controls device functions and stores data acquired by device 12 in memory 34 for transmission to hub 14. Control processor 32 may be embodied as a microprocessor or any other type of control circuitry such as a digital state machine, application specific integrated circuitry, or other circuitry or combination thereof. Memory 34 stores physiological signal data and stores operating parameters and algorithms used by control processor 32.

Power supply 36, which may be a rechargeable battery, provides power for the various circuitry included in device 12. Communication circuitry 38 includes a transmitter, receiver, which may be combined as a transceiver device, and antenna as needed for wirelessly receiving and transmitting data via communication link 20 with communication hub 14. Communication circuitry 38 is normally powered off via switch 40 and will be transitioned from a low power state, which may be an "off" state in which no power is provided to communication circuitry 38, until control 32 causes power supply 36 to provide power to communication circuitry 38 via switch 40. A clock signal 46 or other timing circuitry is included for use in controlling power supplied to the communication circuitry 38 according to scheduled or timed intervals.

Device 12 may include a manual wake up element 41 that may be activated by magnetic field generated by an external magnet or other handheld device. Manual wake up element 41 may be implemented as a reed switch or other zero-power element that generates an interrupt signal in response to an applied field such as a magnetic field generated by the proximity of a magnet or other externally applied field source. The interrupt signal is applied to control 32 to indicate an immediate communication request by hub 14 or external device 16. In response to an interrupt signal generated by manual wake up element 41, control processor 32 will enable power supply 36 to provide power to communication circuit 38 via switch 40. Activation of manual wake up element 41 causes a transition from an off state to an on state of communication circuitry 38 in which a communication link 20 may be subsequently established and data may be transmitted or received by communication circuitry 38.

Transducer 30 or another dedicated implant condition sensor and/or electrodes 42 and 44 and control processor 32 may be configured to cooperatively detect an implant condition or a calibration condition. For example, electrodes 42 and 44 may be used to detect a low impedance signal resulting from contact with bodily fluids or saline. As will be further described herein, the communication circuit 38 may remain in an off state until an implant or calibration condition is detected by an implant/calibration condition sensor, at which time the receiver in communication circuit 38 is powered up for receiving instructions. In the embodiment shown, electrodes 42 and 44 function as an implant condition sensor. In other embodiments, transducer 30 used in monitoring a physiological signal after implantation of sensing device 12 may be used to detect an implant or calibration condition. In still other embodiments, another dedicated zero-power or ultralow power sensor may be provided for detecting an implant condition, which may relate to temperature, pressure, light, etc.

Communication hub 14 includes control circuitry embodied as processor 52 and associated memory 54, communication circuit 58 including transmission and receiving circuitry, and a power supply 56. A timer or clock signal 60 is used for establishing scheduled data transmission times between hub 14 and device 12. Hub 14 may include a reed switch or other manual wake-up element 63 responsive to an external magnet 18 or other handheld device for generating an interrupt signal to control 52. The wake-up interrupt signal indicates an immediate communication request by external device 16. Control 52 provides power to communication circuit 58 via switch 62 to receive instructions from external device 16 and respond accordingly.

At other times, communication link 20 between sensing device 12 and hub 14 is established at a scheduled time under the control of sensing device control 32 and hub control 52. Clocks 46 and 60 may each include an oscillator that provides a periodic interrupt signal to respective control processors 32 and 52 during a beacon listening mode of operation. A beacon signal is generally a higher power communication request signal transmitted by a requesting device beyond the receiver detection limit of the receiving device so that the receiver can operate at a relatively lower sensitivity between communication sessions to save power and to minimize false wake ups due to environmental signals. Reception of a beacon signal is an indicator to initiate a standard communication protocol required for transmitting and receiving data. The periodic interrupt signal causes control processor 32 or 52 to enable respective communication circuit 38 or 58 to periodically listen for a beacon signal from another device indicating a request to establish communication. In response to receiving a beacon signal, control 32 or 52 enables communication circuit 38 or 58 to send and receive data.

Figure 3:
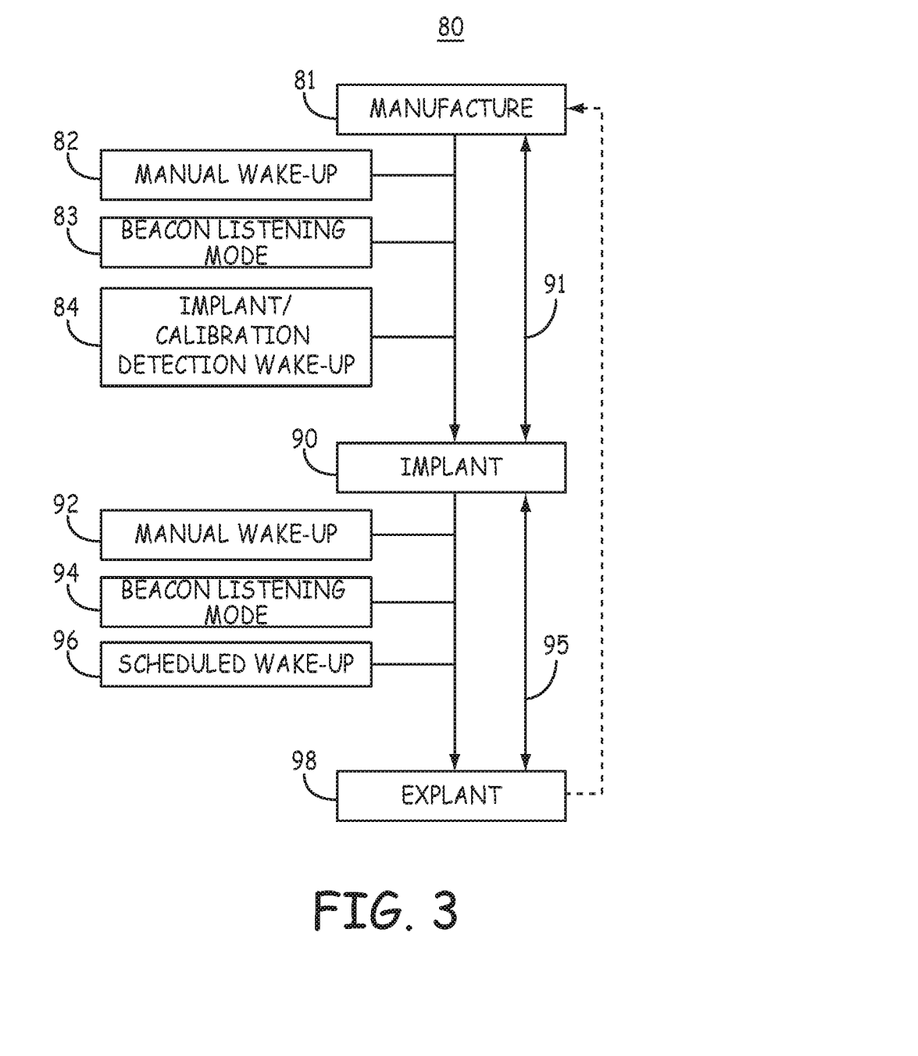
FIG. 3 is a diagram of one embodiment of a communication power management scheme for implementation in an implantable sensing device.

FIG. 3 is a diagram 80 of one embodiment of a communication power management scheme for implementation in conjunction with an implantable sensing device. Diagram 80 shows communication wake-up modes that may be implemented during different time periods 91 and 95 of the sensing device life. Generally, a "shelf-life" period 91 exists from the time of device manufacture 81 until a time of device implant 90. Following the shelf life 91, an implant period 95 exists from the time of implant 90 until a time of explant 98, or until the end of the usable life of the device.

In some embodiments, the sensing device may be a single use device and upon reaching end-of-life or explantation, the device is no longer used. In other embodiments, the sensing device may be a reusable device that is explanted at 98 and is returned (as indicated by dashed arrow) to an initial status that corresponds to settings established at a time of device manufacture 81. As such, in some embodiments the sensing device will operate in a shelf life mode during period 91a single time and in a monitoring or implant mode during period 95 a single time. In other embodiments, a sensing device may operate in a shelf life mode and an implant mode repeated times when the device is reused in the same or different patients.

During the shelf life period 91, the sensing device is configured to operate in at least one of three possible communication wake-up modes. As used herein, a "communication wake-up mode" refers to the method by which the communication circuitry is woken up from a "sleep" state, in which power is not coupled to the sensing device communication circuitry, to an "awake" state, in which the communication circuitry is fully powered for bidirectional communication with the communication hub.

During the shelf life 91, a manual wake-up mode 82 may be enabled which allows a user to manually activate a manual wake-up element in the sensing device to deliver an interrupt signal to the control processor, which in turn powers up the sensing device communication circuitry. The communication circuitry may be powered up directly in response to a manual wake-up interrupt signal or indirectly by first enabling a beacon listening mode 83 as will be described further in conjunction with FIG. 6.

During the shelf life 91, a sensor for detecting an implant or calibration condition may be enabled to cause a wake-up interrupt signal for an automated wake up mode 84 that does not require user intervention. The wake-up interrupt signal provided by an implant/calibration sensor detecting an implant or calibration condition may cause the sensing device control processor to wake up the communication circuitry directly or indirectly by first enabling beacon listening mode 83, as will be described in conjunction with FIG. 6.

A beacon listening mode 83 may be enabled from the time of device manufacture 81 or enabled as part of a manual wake-up mode 82 or automated implant/calibration detection wake-up mode 84. These three communication wake-up modes 82, 83 and 84 may be implemented alone or in any combination during the shelf life period 91. Generally, the communication wake-up mode implemented during the shelf life of the device is used to wake up the sensing device communication circuitry at the time of implant 90 to enable programming, implant measurements or other operations that require communication with the sensing device during the implant procedure.

At the time of implantation 90, the communication wake-up mode is converted to a mode or combination of modes used for the implant period 95. The wake-up mode during the implant period 95 is controlled at least in part by the communication hub. The wake-up mode utilized may vary over the implant period 95 according to instructions received from the hub.

The wake-up mode that is used during the implant period may include the manual wake up mode 92, the beacon listening mode 94, and a scheduled transmission wake-up mode 96 or any combination thereof. The manual wake up mode 92 may be used to wake up the communication circuitry in response to user activation, either directly or indirectly via initiation of a beacon listening mode. During a scheduled transmission wake-up mode, a scheduled wake-up time is programmed in response to a command from the communication hub and causes the sensing device control processor to wake up the communication circuitry directly at the scheduled time or indirectly via initiation of a beacon mode at the scheduled time. The beacon listening mode 94 may be enabled in response to a manual wake-up interrupt, in response to a command from the communication hub, or in response to a scheduled wake-up time. The communication wake up modes 92, 94 and 96 may be enabled singly or in any combination during implant period 95.

An implant/calibration detection wake-up mode 84 is not used after implant 90, i.e. during implant period 95. Generally once implanted, an implant sensor would continuously detect implantation. Once implantation is detected and causes the communication circuitry to be powered up, the implant/calibration detection wake-up mode 84 is disabled from further use during the implant period 95. Other wake-up modes are utilized during the implant period 95 as indicated.

Figure 4:
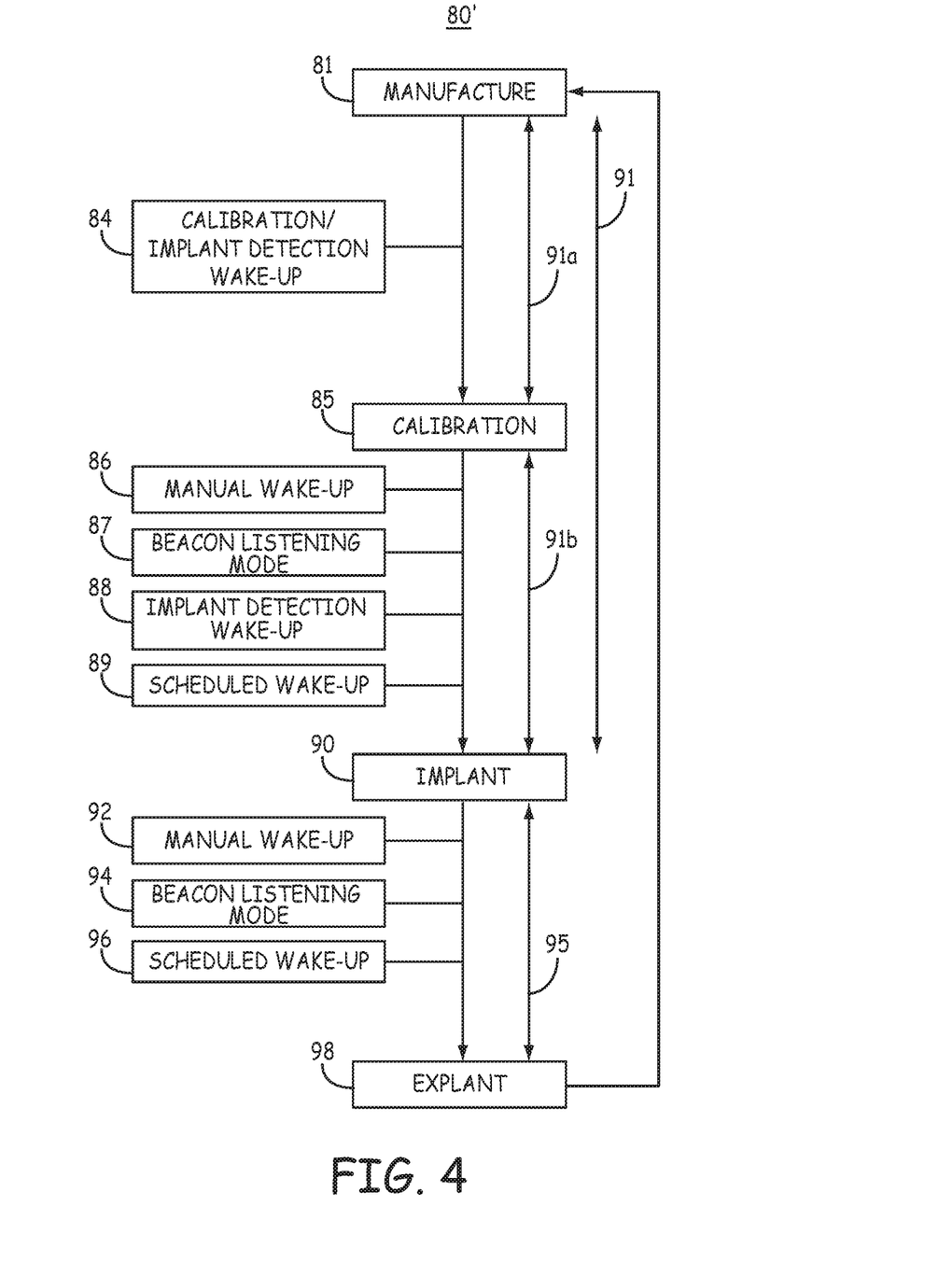
FIG. 4 is a diagram of a communication power management scheme that may be implemented in an implantable sensing device according to an alternative embodiment.

FIG. 4 is a diagram 80' of a communication power management scheme for use in an implantable sensing device according to an alternative embodiment. In FIG. 3, it is assumed that if any device calibration needs to be performed, it is performed at a time of device manufacture 81 or at the time of implant 90. In FIG. 4, a calibration 85 may be performed at a separate point in time from manufacture 81, when the battery is electrically coupled to other sensing device circuitry, and at a separate time from implant 90. Different wake-up modes may be utilized during different portions 91a and 91b, prior to calibration and after calibration, respectively, of a shelf life 91.

In some embodiments, it may be desirable to minimize the likelihood of false wake-ups and power usage during the shelf life 91. This can be done by disabling the manual wake-up mode and/or the beacon listening mode during at least a portion of the shelf life of the sensing device. The calibration/implant detection wake up mode 84 may be enabled as the sole wake-up mode during a shelf life portion 91a extending from the time of device manufacture 81 until a time of device calibration 85 (or throughout shelf life 91).

In some embodiments, a calibration procedure may be performed in a simulated implant environment, such as in a saline solution, a temperature controlled chamber, a pressure-controlled chamber, or the like. Thus detection of a calibration condition corresponding to a simulated implant condition by the sensing device may cause the device communication circuit to be enabled, for example in a beacon listening operating mode. After completing a calibration procedure, the hub 14 or another external device may program calibration constants for storage by the sensing device. The sensing device either automatically or in response to further instructions shuts down power to the communication circuitry and disables the beacon listening mode until an implant condition is detected again. Power may be conserved during the post-calibration period 91b by putting the communication circuitry to sleep until an implant condition is detected.

The time of device calibration 85 may occur at varying intervals 91a and 91b from the time of device manufacture 81 and the time of device implantation 90, respectively, depending on the type of device and other factors. The wake-up mode during the second portion 91b of the shelf life period, between calibration 85 and implantation 90 of the device, may include one or more of wake-up modes 86, 87, 88 and 89 and may use a different mode(s) than the communication mode used during the first portion 91a of the shelf life period. The communication mode set for the post-calibration/pre-implant interval 91b may be established by the communication hub (or another programming device) at the time of calibration 85 and based in part on the expected duration of the time period 91b.

For example, if calibration 85 occurs soon after device manufacture 81, such that the period of time 91b until implant is still relatively long, the hub may send a command to re-enable the calibration/implant detection wake-up mode 88 that will cause communication circuitry to be powered up only in response to an implant condition being detected. The manual wake up mode 86, the beacon listening mode 87, and the scheduled wake-up mode 89 may be disabled during this time to reduce the likelihood of false wake-ups and minimize power usage.

In another example, if calibration 85 occurs at a very short period of time before implant 90, the beacon listening mode 87 or even a scheduled wake-up mode 89 may be enabled after calibration 85. As such, if calibration 85 does not occur at substantially the same time as device manufacture 81 or device implant 90, a different mode or combination of communication wake-up modes 86, 87, 88 or 89 may be selected to set the overall wake-up mode used during a post-calibration, pre-implant period of time 91b, which may be different than one or both of the wake-up modes during the pre-calibration shelf life period 91a and the implant period 95.

The sensing device is converted to a communication wake-up mode that includes any combination of manual wake-up mode 92, beacon listening mode 94, and scheduled transmission wake-up mode 96 during implant period 95. Wake-up modes 92, 94 and 96 may be implemented alone or in any combination during implant period 95 and the implemented wake-up mode may change over time during implant period 95 as controlled, at least in part, by the communication hub 14.

Figure 5:
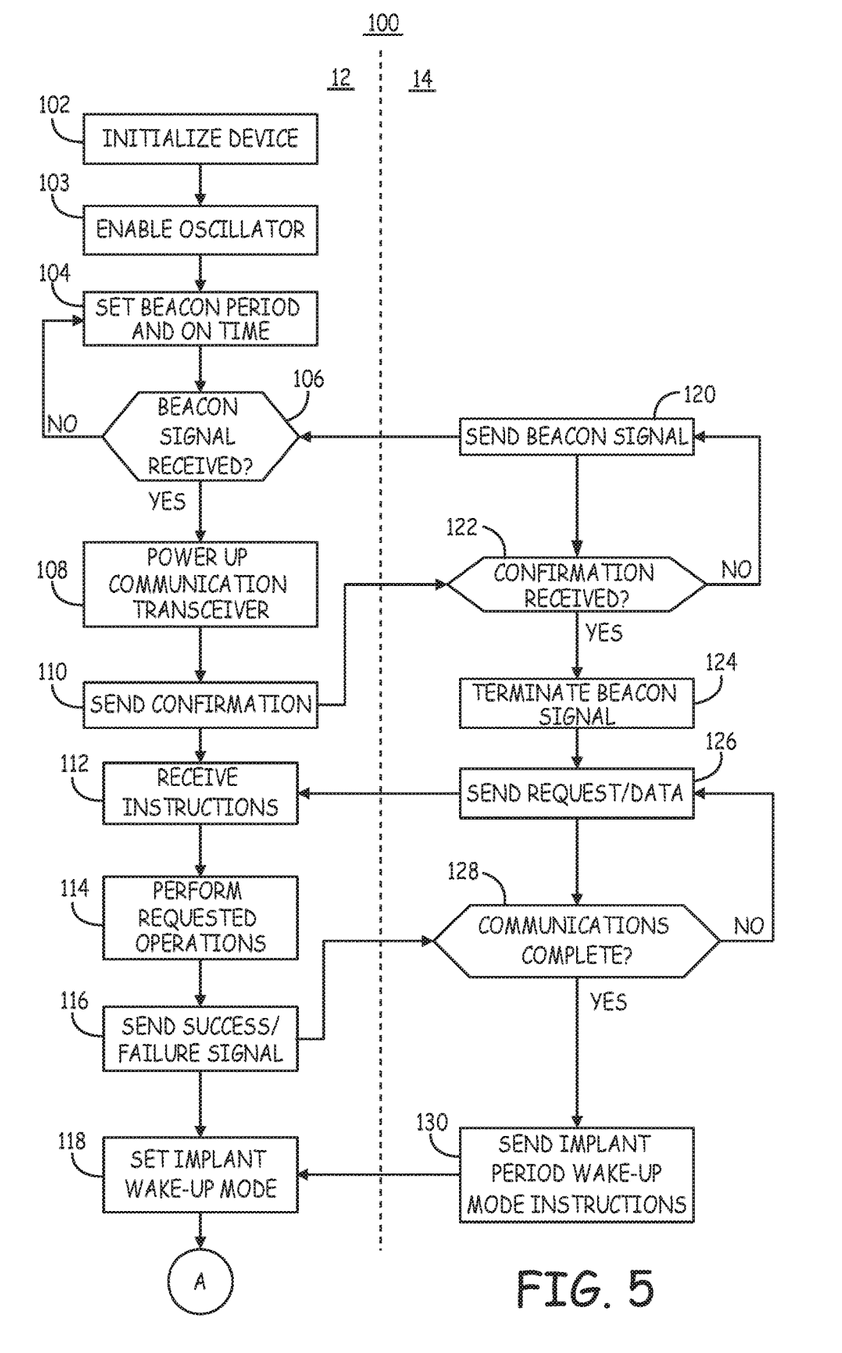
FIG. 5 is a flow chart of one method for power management of communication operations in an implantable sensing device during its shelf life.

FIG. 5 is a flow chart 100 of one method for controlling communication power in a medical device system during a shelf life period of an implantable sensing device. Operations performed by or pertaining primarily to sensing device 12 are shown on the left side of the dashed line and operations performed by or pertaining primarily to the communication hub 14 are shown on the right side of the dashed line.

Flow chart 100 and other flow charts presented herein are intended to illustrate the functional operation of the associated devices, and should not be construed as reflective of a specific form of software or hardware necessary to practice the methods described. It is believed that the particular form of software will be determined primarily by the particular system architecture employed in the device. Providing software to accomplish the described functionality in the context of any modern implantable medical device system, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The method shown by flow chart 100 pertains to power management operations during the "shelf-life" of the sensing device 12, i.e. during a time period between device manufacture and implantation of the sensing device 12 in a patient's body. In this embodiment, sensing device 12 is configured to operate in a beacon listening wake-up mode at the time of device manufacture and throughout the shelf life of the device and is then converted to a desired communication wake-up mode for an implant period during an implantation procedure.

At block 102 the sensing device is initialized at the time of device manufacture. Initializing the device includes setting a power status for the shelf life of the device. Power supplied to sensor transducer circuitry or other functional circuitry not used or needed during storage of the device is disabled. However, the sensing device is initialized to enable power to a transceiver in the communication circuit periodically. In one embodiment, the sensing device is provided with an ultralow power oscillator that is enabled at block 103 to periodically generate an interrupt signal provided to the sensing device control circuitry. In response, the control circuitry enables a switch to provide power from the sensing device power supply to the communication transceiver in the sensing device. This periodic interrupt signal is enabled at block 103 at the time of device initialization to cause a periodic wake-up of the transceiver to "listen" for a beacon signal during its shelf life.

At block 104 a beacon period and on time are set. The beacon period defines the oscillation period of the beacon listening interval, i.e. how often the transceiver is powered up to listen for a beacon signal. The beacon on time defines how long the transceiver will remain powered up to listen for a beacon signal before it is powered down again. For example, the oscillator may be enabled to provide an interrupt signal to the communication transceiver approximately once per second, once per minute, every two minutes, every five minutes or other set time interval (the beacon listening period). The on time will be a fraction of the beacon listening period, for example, a fraction of a second, a fraction of a minute, and so on.

Between beacon listening intervals, power is largely conserved because the oscillator is an ultralow power oscillator, which may utilize current in the range of the normal leakage current of the device or less. For example, in a miniaturized sensing device having a volume of 1 cc or less, an average current drain for normal sensing function of the device may be on the order of approximately 100 nA. An ultralow current drain would be a fraction of the normal function current drain, for example approximately 10 nA or less, which may correspond to an ultralow power of approximately 30 nW or less for a 3V supply.

At block 106, the sensing device listens for a beacon signal during the on time that is initiated at the start of each beacon period. If no beacon signal is received before expiration of the on time, the communication circuitry is powered down until the start of the next beacon period (return to block 104).

At the time of sensing device calibration and/or device implantation, the communication hub 14 is enabled (for example manually) to transmit a beacon signal at block 120. The beacon signal may be transmitted for a period of time that is at least as long as the beacon period plus the on time set in the sensing device to promote reception of the beacon signal by the sensing device during the next on time. If a confirmation signal from the sensing device is not received at block 122 by the hub 14, the process in hub 14 returns to block 120. The beacon signal may be sustained or extended, rescheduled, and/or increased or otherwise adjusted in power in another attempt to establish communication with the sensing device 12.

If a beacon signal is received by the sensing device 12, the sensing device control circuitry fully enables the communication transceiver by providing power at block 108 so that data may be received/transmitted. The communication transceiver may remain enabled to receive/transmit data until a power-down or "sleep" command is received or until no communication occurs for a predetermined period of time.

A confirmation signal is returned to the hub 14 at block 110. If the communication is a full duplex mode between the sensing device 12 and hub 14, sensing device 12 can immediately send a beacon response signal at block 110 confirming that a communication link is established and the receiver is ready to receive data. The hub 14 can then terminate the beacon signal at block 124 to save energy in hub 14. If the communication mode between sensing device 12 and hub 14 is half-duplex, the sensing device 12 will wait for the termination of the beacon signal and then send the beacon response signal immediately afterwards at block 110.

Sensing device 12 receives instructions from hub 14 at block 112 and performs any requested tasks at block 114. Instructions received at block 112 may include operating commands to perform measurements or transfer data, clear memory registers, store calibration data, store a monitoring protocol, or the like. After receiving a complete data transmission and implementing new operating parameters or completing requested tasks at block 114, the sensing device may send a success signal at block 116 back to hub 14.

Requested tasks performed at block 114 may involve additional bidirectional communication not explicitly shown in FIG. 5 between device 12 and hub 14 such as transmitting sensed signal data. If received data is incomplete or other errors occur, a failure signal may be transmitted by sensing device 12 at block 116.

Hub 14 determines if all communications are complete at block 128. In response to a failure signal sent by the sensing device 12, hub 14 returns to block 126 to resend data and/or make additional requests. If a success signal is received by hub 14, additional communication operations may still be required depending on the particular tasks being performed. As such, if communications are not complete according to a particular calibration or implantation protocol, hub 14 may return to block 126 to send additional data to sensing device 12.

If communications are determined to be complete at block 128, the communication hub sends instructions establishing a wake-up mode for the subsequent implant period at block 130. In some embodiments, determining that communications are complete may be automatic by hub 14. In other embodiments, a manual command entered by a user using an external device in communication with hub 14 may indicate that communication operations are complete.

In response to the wake-up mode instructions transmitted from hub 14 to sensing device 12, the sensing device enables an implant period wake up mode at block 118 according to the received instructions. For example, the oscillator providing a control interrupt signal to periodically wake-up the communication transceiver to listen for a beacon signal may be disabled and a scheduled time may be set for waking up the communication circuitry, either directly or via re-enabling the beacon listening mode. In this way, a continuous beacon signal listening mode is enabled only prior to and up to implantation of the device, i.e., during the shelf-life of the device, in some embodiments such that communication may be initiated with the sensing device 12 when needed to perform calibration operations, perform implant testing and measurements, and/or confirm a desired implant location.

After implantation, the sensing device is configured to conserve power by operating in a wake-up mode established by the communication hub 14. Sensing device operation proceeds to a monitoring or implant mode of operation, as indicated by connector A, which is generally described below in conjunction with FIG. 7. It is understood that at any time during the shelf life of the sensing device 12, the sensing device communication circuitry may be powered up in response to manual activation of a manual wake-up element, such as a magnet applied to a reed switch in the sensing device, as described previously.

It is contemplated that in some embodiments, a beacon listening mode of operation is restored after performing calibration procedures and maintained until an implantation procedure is performed. As such, in some embodiments, the beacon listening mode may be initialized at device manufacture, used to establish communication with a hub to perform a calibration procedure, then restored and maintained until communications are again established during an implantation procedure. When the communication transceiver is powered up at block 108, the beacon listening mode is disabled temporarily but may be re-enabled after calibration procedures are completed until an implant procedure is performed at a later time.

Figure 6:
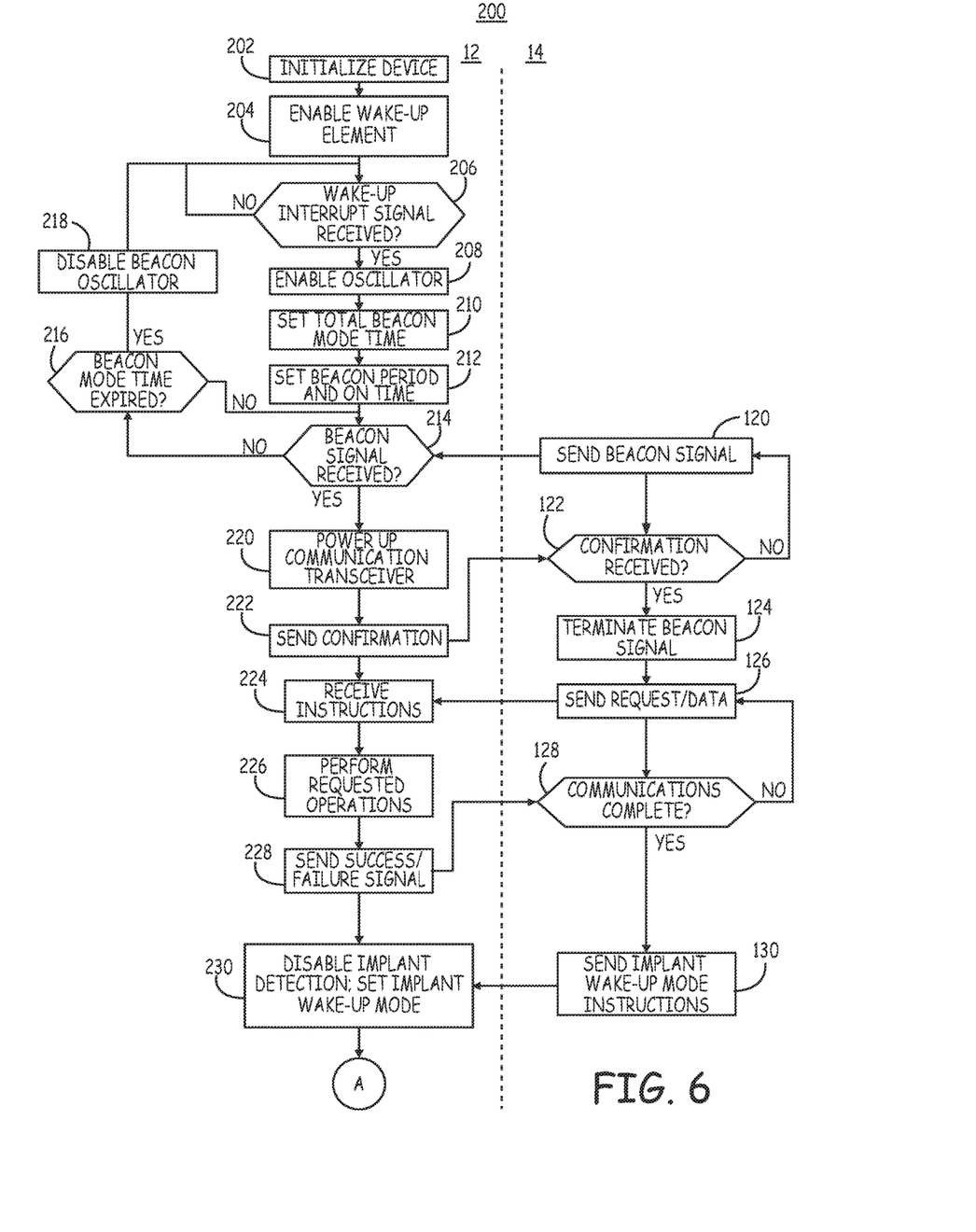
FIG. 6 is a flow chart of an alternative method for power management of communication operations in an implantable sensing device during its shelf life.

FIG. 6 is a flow chart of an alternative method for power management of communication operations in an implantable sensing device during its shelf life. In flow chart 200, instead of enabling a beacon listening mode of operation at the time of device manufacture, a "wake-up" element is provided for first detecting a wake-up condition, which causes the beacon listening mode to then become enabled.

At block 202, the sensing device 12 is initialized at the time of device manufacture by setting any default programmable parameter values and setting a power status of the device for the shelf-life of the device. Power supplied to sensor circuitry not used or needed during storage of the device is disabled. The power status includes shutting down power to the sensing device communication circuit and the oscillator generating an interrupt signal for the beacon listening mode. The communication circuit and beacon mode oscillator remain completely powered down until an implant or calibration condition is detected.

Device initialization includes enabling a wake-up element at block 204. The wake-up element may correspond to a zero-power or ultra-low power manual wake-up element, such as a reed switch that responds to user application of a magnet to the sensing device. Additionally or alternatively, the "wake-up element" enabled at block 204 may correspond to a zero-power or ultra-low power implant sensor configured to automatically detect an implant or calibration condition. In one embodiment, the sensing device is configured to detect an implant condition by performing periodic impedance measurements taken between electrodes on the sensor housing. A periodic current signal is applied to the electrodes and the resulting voltage across the electrodes is measured to determine an impedance measurement. If the impedance remains high due to an air path between electrodes, for example while still in a package prior to implantation, an implant or calibration condition is not detected. The sensing device remains in the power status set for the shelf-life of the device as indicated by the "no" loop of block 206.

The impedance may be monitored by continuous or intermittent cycling of a low level current signal to the impedance measuring electrodes with the resulting voltage provided as input to a comparator for detecting a low impedance between the electrodes. One impedance monitoring method for implant detection is generally described in U.S. Pat. No. 5,534,018 (Wahlstrand, et al.), hereby incorporated herein by reference in its entirety. In an alternative embodiment, a temperature measurement method may be employed for detecting device implantation, as generally described in U.S. Pat. No. 6,681,135 (Davis, et al.), hereby incorporated herein by reference in its entirety.

A zero-power or ultra-low power wake-up element implemented to sense or respond to a wake-up condition and generate a wake-up interrupt signal uses minimal current from the sensing device power supply. A minimal current may be on the order of the leakage current of the sensing device or less, and may correspond to a current drain of up to approximately 100 nA and may be less than approximately 1 nA.

If a wake-up element detects a calibration or implant condition, or a manual wake-up element is activated, the sensing device control processor receives a wake-up interrupt signal generated by the wake-up element at block 206. The sensing device control processor enables a beacon listening mode oscillator at block 208. Upon enabling the beacon listening mode oscillator, sensing device 12 sets a total beacon mode time at block 210. The beacon listening mode will be enabled for a maximum period of time and will then be disabled again. This maximum beacon listening mode time prevents the sensing device from remaining in a beacon listening mode indefinitely due to a false wake-up.

The beacon period and on time are set at block 212 as described previously to enable the sensing device to periodically listen for a beacon signal from the hub 14, signifying a request for communication by the hub, during the total beacon mode time. If no beacon signal is received during an on time interval at block 214 and the beacon mode time expires, as determined at block 216, the beacon listening mode is terminated at block 218 by disabling the oscillator interrupt signal. The sensing device control processor returns to block 206 to wait for another wake-up interrupt signal generated by a calibration/implant detection element or a manual wake-up element.

If the hub sends a beacon signal at block 120, and the signal is received by sensing device 12 at block 214 during the beacon on time, the sensing device communication circuit is powered up at block 220. The behavior of hub 14 at block 120 through 130 corresponds to that described in conjunction with FIG. 5. Once a beacon signal is received, the behavior of sensing device 12 at blocks 220 through 228 generally corresponds to that described in conjunction with blocks 108 through 118 of FIG. 5.

Briefly, the communication hub 14 sends instructions or requests to the sensing device 12 at block 126 after receiving a confirmation from sensing device 12 and terminating the beacon signal (block 222 and blocks 122-124). Upon receiving the instructions at block 224, the sensing device 12 performs the requested operations at block 226 and sends a success signal at block 228. When communications are complete (block 128), e.g. calibration procedures, implant measurements, initial programming of the sensing device and so on, instructions establishing a communication wake up mode to be enabled during the subsequent implant period are sent (block 130).

At block 230, the sensing device enables the communication wake-up mode for the implant period according to the received instructions. In one embodiment this includes enabling a scheduled transmission wake-up mode. An implant detection wake-up mode is disabled at block 230. Once a device is implanted, the circuitry used for detecting an implant or calibration condition may be completely powered down. The implant detection wake-up interrupt signal is disabled and not used for the duration of the implant life of the device.

Figure 7:
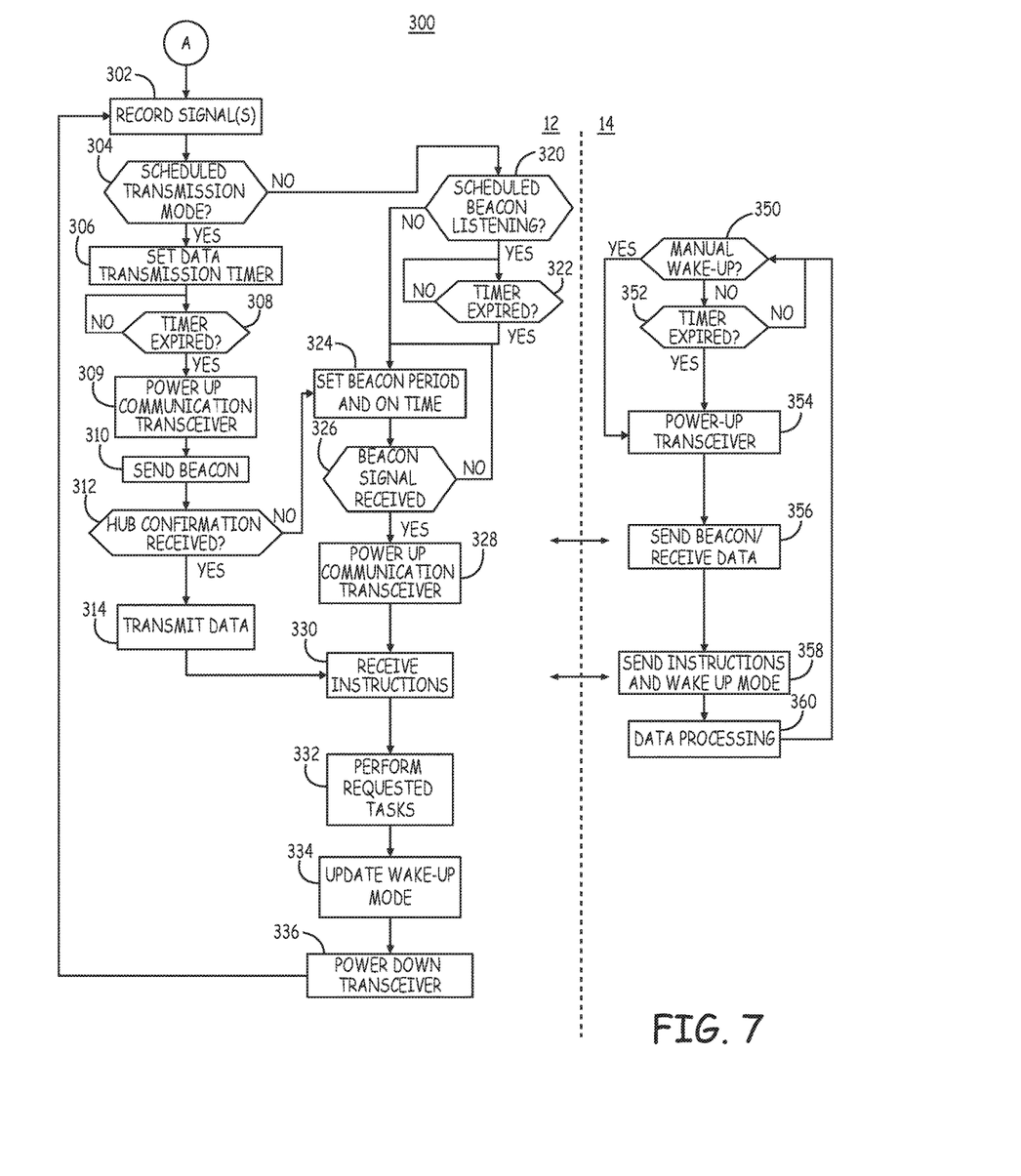
FIG. 7 is a flow chart of one method for controlling communication functions of an implantable sensing device enabled to perform a monitoring protocol according to one embodiment.

Sensing device operation proceeds to a monitoring mode of operation, as indicated by connector A, as generally described in conjunction with FIG. 7. The sensing device 12 may perform sensing operations according to a monitoring protocol, but no communication data will be sent or received until the sensing device communication circuitry is woken up according to an implemented wake-up mode.

While the methods of a beacon listening mode and a wake-up element detecting a wake-up condition are described in a combined manner in conjunction with FIG. 6, it is contemplated that a sensing element included in sensing device 12 for detecting a wake-up condition may be implemented without a beacon listening mode operation. In response to sensing an implant condition or manual wake-up activation, the sensing device communication circuitry may be fully powered up to enable bidirectional communication with hub 14 and remain powered up until further instructions are received by hub 14. Additionally, a timer may be set for powering down the sensing device communication circuitry if data is not received from hub 14 during a specified time period after sensing the implant condition to avoid sustained power to the communication circuitry due to a false wake up.

FIG. 7 is a flow chart 300 of a method according to one embodiment for managing communication power usage in an implantable medical device system enabled to perform a monitoring protocol. Flow charts 100 and 200 of respective FIGS. 5 and 6 relate to sensing device communication operations and power management during the shelf-life of the sensing device. The flow chart 300 of FIG. 7 relates to the control of communication functions during the implant period. Operations performed by or pertaining primarily to sensing device 12 are shown on the left side of the dashed vertical line and operations performed by or pertaining primarily to the communication hub 14 are shown on the right side of the dashed vertical line as indicated.

After setting an initial communication wake-up mode at the end of the shelf life, i.e. upon implantation, as described above, the sensing device 12 begins to function according to a programmed monitoring protocol for recording a physiological signal (or signals). The sensing device 12 may be configured in an ultralow power or off state between physiological signal monitoring intervals to conserve power.

If the initial communication wake-up mode set for the implant period is a scheduled transmission wake-up mode, as determined at decision block 304, a scheduled wake-up interval timer is set at block 306 for a data transmission time established by the communication hub 14 when the communication wake-up mode was set. When the scheduled transmission timer expires, as determined at block 308, sensing device 12 powers up its communication circuitry at block 309 and transmits a beacon signal at block 310 to request communication with hub 14.

When operating in a scheduled transmission wake-up mode, the hub 14 may operate in a beacon listening mode. Alternatively, the hub may set a hub wake-up timer for enabling a beacon listening mode at a particular time. In this way, the communication circuitry of the hub 14 may be powered down between scheduled data transmission times.

At any time, however, an external wake-up activation signal may be applied to the hub 14 to activate a manual wake-up element included in hub 14. If the manual wake-up element is activated at block 350, a manual wake-up interrupt signal is generated to cause the hub to power up its transceiver at block 354. The hub 14 may then begin sending a beacon signal and/or listening for a beacon signal from sensing device 12 for establishing communication with sensing device 12.

While not explicitly shown in FIG. 7, it is to be understood that sensing device 12 may be configured for manual wake-up capabilities at any time during the implant life of the device, as described previously herein.

If a scheduled transmission wake-up timer expires at block 352 in hub 14, the hub transceiver is powered up at block 354. The scheduled wake-up interval set in hub 14 expires at a somewhat shorter interval than the sensing device scheduled wake up interval. As a scheduled transmission time approaches, the communication hub transceiver is woken up earlier, for example one second, one minute or even earlier than the scheduled wake up time of the sensor. Mismatches between timing circuits of the hub and the sensing device are accommodated by enabling the communication hub 14 to listen for a beacon signal from the sensing device 12 at a slightly earlier time than the sensing device wake-up time. If the communication hub receiver is enabled at a scheduled time that is intended to correspond exactly to a scheduled transmission time of the sensing device, a mismatch between timing circuits of the hub 14 and sensing device 12 could cause communication errors or failures.

Upon receiving a confirmation from the hub 14 at block 312, the sensing device 12 begins transmitting acquired data at block 314, which may be stored or real-time data depending on the monitoring application. In an alternative embodiment, the sensing device transceiver may be powered up upon expiration of a scheduled wake-up time interval and immediately begin transmitting data at block 314 without first sending a beacon signal and waiting for a response. In this case, the hub 14 would fully power-up its communication circuitry in advance of the scheduled transmission time.

The communication hub 14 receives the sensing device data at block 356. With the reception of data, the hub 14 can trim its internal oscillator to compensate for drifts between the timing circuits of the hub 14 and the sensing device 12.

After receiving a complete data transmission from sensing device 12, communication hub 14 sends instructions, including instructions relating to the communication wake-up mode, to the sensing device 12 at block 358. The sensing device 12 may enable communication error correction protocols, receive updated operating parameters, or receive other information back from the hub 14 at block 330. The hub may send instructions regarding additional tasks to be performed by the sensing device, which are performed at block 332 and may involve additional bidirectional communication with hub 14. The communication wake-up mode is updated at block 334 according to the received instructions.

The communication wake-up mode may remain unchanged, or the wake-up mode may be converted to a different mode, for example from a scheduled transmission mode to a scheduled or continuous beacon listening mode. Furthermore, time intervals used to control the wake-up mode may remain the same or be changed. The wake-up mode and/or intervals used to control wake-ups may change depending on a physiological status of a patient, a therapy delivery status, or based on user input.

If a scheduled transmission wake-up up mode is maintained, the hub may provide an instruction to keep the same or set a different scheduled transmission wake-up interval. In one embodiment, the next wake-up interval scheduled in the sensing device after a data transmission is a relatively short wake-up interval that corresponds to a data processing time in hub 14. The sensing device sets the wake-up timer at block 306 and powers down the communication circuitry until the timer expires, as determined again at block 308. Additionally, the sensing device may disable power to any sensing operations during this data processing time.

The scheduled wake-up interval transmitted at block 358 in this case may be referred to as a processing time wake-up interval in that this interval is not set to establish the next time that the sensing device is scheduled to transmit acquired physiological signal data. Rather this processing time interval is a time period in which the signal data just transmitted by sensing device 12 is analyzed by hub 14 at block 360. Sensing device 12 may or may not acquire physiological data during the processing time interval. The communication circuitry of the sensing device 12 is shut down during data processing to conserve device power. The data analysis performed during the processing time interval is used to establish the next scheduled wake-up interval that defines when a data transmission will again occur.

The hub 14 determines a next scheduled transmission wake-up time interval based on the data analysis and transmits the next wake up time interval to the sensing device 12 at the next scheduled wake-up time. In response to the processed data, the hub may increase, decrease, or maintain a previous wake-up time interval used for transmitting sensed data. For example, if the sensed signals indicate that the patient is stable, the wake-up interval for the next data transmission time may remain the same or be increased. If the sensed signals indicate that a condition may be changing or unstable, the wake-up interval for the next data transmission may be shortened to allow more frequent monitoring of physiological data.

It is recognized that in some embodiments, data processing at block 360 may be performed by another device after transferring the received data from hub 14 to the other device, which may be implanted or external. The external device 16 communicates a wake-up schedule back to hub 14 for subsequent transmission to the sensing device 12.

The communication transceiver of the sensing device 12 is powered up at block 309, at the end of the scheduled wake-up interval corresponding to a data processing time, to receive the next scheduled transmission wake up time from the communication hub. At this time, there may be no new physiological data to transmit so after sensing a beacon signal at block 310 the sensing device may wait for wake-up mode instructions. The next scheduled wake-up time will correspond to a time interval that will include further monitoring by the sensing device for acquiring physiological signal data.

At other times, the wake-up mode may be converted to a continuous or scheduled beacon operation. If the wake-up mode is not a scheduled transmission mode (block 304), the wake-up mode may be a scheduled beacon listening mode, as determined at block 320. Configuring a scheduled beacon listening mode includes setting a timer for the first beacon listening period to begin.

When the timer expires at block 322, the beacon period and beacon on time are set at block 324. The beacon period sets the period at which an oscillator provides a wake-up interrupt signal to the sensing device control circuitry. The on time controls how long the communication circuitry is powered and enabled to listen for a beacon signal during a given beacon period. If a signal is not received during an on time, the device returns to block 324 and remains in a beacon listening mode until a beacon signal is received at block 326.

If the wake-up mode is neither a scheduled transmission mode (block 304) or a scheduled beacon listening mode (block 320), the wake-up mode is set to a continuous beacon listening mode. The process advances to block 324 where the beacon period and on time are set to repeatedly cause a periodic wake-up interrupt signal and beacon listening on time until a beacon signal is received during an on time at block 326.

Additionally, if a scheduled transmission wake-up mode is set but a hub confirmation signal is not received at block 312 after sending a beacon signal at block 310, this failure to establish communication can cause the wake-up mode to automatically convert to a continuous beacon listening mode by advancing to block 324. The "continuous" beacon listening mode is "continuous" in that no timer is set to separate beacon periods. The beacon period and on time are set during the "continuous" beacon listening mode such that the communication circuitry is shut down during an "off time" portion of the beacon period, which corresponds to the time period from the end of an on time until the next wake-up interrupt signal is provided by the oscillator.

If a beacon signal is received at block 326, the communication transceiver is fully powered at block 328 for establishing bidirectional communication with the hub 14. The sensing device 12 may send a confirmation signal to the hub 14 and data transmission may then begin between the device 12 and hub 14 in a handshaking mode.

After receiving instructions and performing any requested tasks at blocks 330 and 332, the sensing device wake-up mode is updated at block 334 according to hub instructions. Sensing device communication circuitry is put to sleep at block 336 and the process returns to block 302 to continue recording physiological signals per a programmed monitoring protocol.

As such, the communication wake-up mode of sensing device 12 may vary between a scheduled transmission mode, a scheduled beacon listening mode, and a continuous beacon listening mode under the control of hub 14 during an implant period. Converting from one mode to another, for example from a scheduled transmission mode to a continuous beacon listening mode, may occur automatically by sensing device 12 in response to a communication failure or other events.

The communication wake-up mode may be implemented as one or a combination of wake-up modes, which may vary over the implant life of the sensing device. For example, in an alternative embodiment, instead of setting a scheduled wake up interval corresponding to a data processing time as described above, a scheduled transmission wake-up mode may be followed by a scheduled beacon listening mode. Beacon listening will be enabled after a scheduled time interval that corresponds to an expected data processing time.

Alternatively, the sensing device may enable a scheduled or continuous beacon listening mode automatically at the end of a scheduled data transmission to wait for instructions regarding the next wake-up mode.

Figure 8:
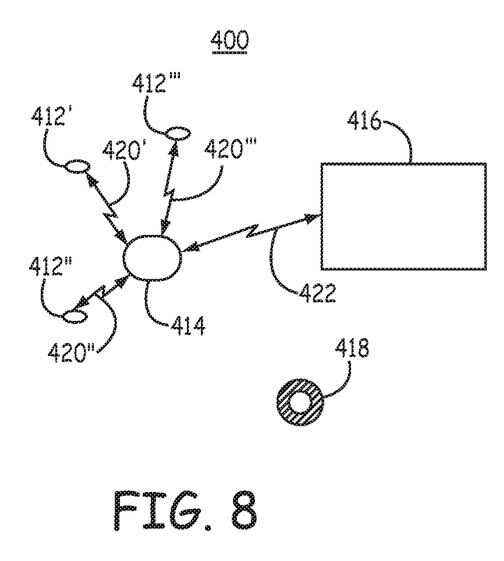
FIG. 8 is a schematic diagram of an implantable medical device system comprising multiple implantable medical devices in bidirectional communication with a communication hub.

FIG. 8 is a schematic diagram of an implantable medical device system including multiple implantable medical devices 412', 412", 412''' (collectively 412) in bidirectional communication with a hub 414 via respective communication links 420', 420" and 420''' (collectively 420). The devices 412 may be embodied as one or more types of sensing devices implanted in distributed locations in a patient's body. Hub 414 provides communication power management for the multiple devices 412 by transmitting a wake-up mode and associated time intervals, e.g. a scheduled transmission wake-up interval, a scheduled beacon listening wake-up time, beacon period, and beacon on time.

Furthermore, external device 416 may program a wake-up mode in hub 414, which may generally correspond to any of the wake-up modes described herein, and a wake-up mode to be transmitted to sensing device(s) 412. Additionally, each device 412 and hub 414 may be woken up by activation of a reed switch or other manually activated ultra-low power or zero-power sensor as described previously. Providing a method for manually causing communication wake up between scheduled wake ups allows emergency or other procedures that require communication with hub 414 and/or any devices 412 to be performed between scheduled wake-ups.

Hub 414 controls the communication power mode of each sensing device 412 by sending commands via an appropriate communication link 420. Hub 414 may manage the communication power used by the devices 412 by determining whether the device operates in a scheduled wake-up mode or in a scheduled or continuous beacon listening mode, and these modes of operation may be changed over time. Hub 414 may determine the communication wake up mode for each device 412 automatically, based on a patient condition and/or the type of signal(s) sensed by the sensing device.

For example, if a sensing device is providing signals relating to confirming an arrhythmia, the sensing device may be set to a continuous beacon listening mode so that data can be quickly retrieved from the sensing device when a serious arrhythmia is detected or suspected. If a sensing device is providing signals relating to a physiological condition that may change more gradually over time, e.g. thoracic edema or other heart failure condition, the sensing device may be set to a scheduled transmission wake-up mode with intervals of beacon listening mode operations following each scheduled transmission and corresponding to data processing time periods.

Hub 414 dynamically controls the communication wake up mode of the devices 412 according to patient need and physician preferences. Hub 414 may select an operating mode for a particular device 412 automatically based on patient condition, sensing device functionality, and other factors. Alternatively or additionally, hub 414 may receive instructions for controlling wake-up modes of the sensing devices 412 from an external device 416. External device 416 is used to transmit programming instructions entered by a user or determined automatically in response to analysis of data received from devices 412. Each sensing device 412 may be controlled to transmit data according to a unique wake up schedule for that device.

The hub 414 may maintain its own communication circuitry in an off state and power up its receiving circuitry in accordance with scheduled wake up times of devices 412 or a scheduled wake up time for communicating with external device 416.

When the magnet 418 is held over hub 414, hub 414 powers up its communication transceiver and waits an interval of time for a wake-up command from external device 416 that identifies the hub with its own unique device identification. If this command is not received, hub 414 shuts down its communication circuitry. The communication circuitry may be locked in response to not receiving a command so that the circuitry cannot be enabled by a manual wake-up mode again for a certain interval of time. This interval of disabling the manual wake up mode prevents frequent powering up of the communication circuitry due to electromagnetic interference or other spurious magnetic fields and may be implemented in the sensing devices 412 and the hub 414 to reduce power losses due to false manual wake-ups.

If the hub 414 does receive the wake-up command containing the hub's unique identification within a predetermined time interval, the hub establishes a communication link 422 with external device 416 and receives programming data and destination information from external device 416. The data is then transferred to the appropriate devices 412.

In a similar manner, any of sensing devices 412 may be woken up using magnet 418 or other manual activator of an internal sensing element that is configured to provide an interrupt signal to control circuitry within the sensing device. The sensing device 412 waits a predetermined interval of time for a command including a unique identity of the sensing device and enables its communication circuitry for receiving further data in response to the command. If the predetermined interval expires before receiving the command, the communication circuitry is prevented from being woken up again by an external signal for a predetermined period of time to prevent power losses to due external interference.

Hub 414 reduces communication power usage by the sensing devices 412 by performing higher power communication transmissions to external device 416 and by establishing the wake-up mode of the sensing devices 412 during the implant period of the device.

Thus, an implantable medical device system and method for managing device communications and associated power usage has been presented in the foregoing description with reference to specific embodiments. It is appreciated that various modifications to the referenced embodiments may be made without departing from the scope of the disclosure as set forth in the following claims.

The invention claimed is:

1. A medical device system, comprising:
a first device comprising a control processor, a first power supply, a physiological sensor for sensing a signal in a patient, and a first communication circuit; and
a second device comprising a second power supply and a second communication circuit configured for bidirectional communication with the first communication circuit;
wherein the control processor is configured to:
provide power from the first power supply to the first communication circuit according to a first communication wake-up mode set for a first time period that corresponds to a pre-implant time period for the first device and according to a second communication wake-up mode set for a second time period that corresponds to a post-implant time period for the first device in the patient, wherein the first communication wake-up mode specifies at least one first communication wake-up condition and the second communication wake-up mode specifies at least one second communication wake-up condition;
detect a first event that satisfies the first communication wake-up condition during the first time period and, in response, provide the power from the power supply to the first communication circuit and establish a first communication session between the first device and the second device, wherein the first communication session occurs during the first time period and is enabled according to the first communication wake-up mode, and wherein, during the first communication session, the first device is configured to receive instructions from the second device to establish the second communication wake-up mode for the second time period; and
detect a second event that satisfies the second communication wake-up condition during the second time period and, in response, provide the power from the power supply to the first communication circuit and establish a second communication session between the first device and the second device, wherein the second communication session occurs during the second time period and is enabled according to the second communication wake-up mode.

2. The system of claim 1, wherein the first communication wake-up mode comprises one of a manual wake-up mode, an implant detection wake-up mode, and a beacon listening mode.

3. The system of claim 1, wherein the second communication wake-up mode comprises one of a scheduled transmission wake-up mode, a continuous beacon listening mode, and a scheduled beacon listening mode.

4. The system of claim 1 wherein the first device comprises a wake-up element for detecting a wake-up condition, wherein the first communication wake-up mode comprises detection of a wake-up condition and enabling a beacon listening mode in response to detection of the wake-up condition.

5. The system of claim 4, wherein enabling the beacon listening mode in response to the wake-up element detecting the wake-up condition is disabled during the second time period.

6. The system of claim 1, wherein the first device comprises a manual wake-up element for generating a wake-up interrupt signal received by the control processor in response to a user intervention, the manual wake-up element being enabled during the second time period and disabled during the first time period.

7. The system of claim 1, wherein the second device is configured to establish the second communication wake-up mode as a scheduled transmission wake-up mode including a time interval for the scheduled transmission, wherein, according to the scheduled transmission wake-up mode, the first device is configured to cause the first communication circuit to transmit a beacon signal to the second device upon expiration of the scheduled transmission time interval.

8. The system of claim 7, wherein the first device is further configured to convert the scheduled transmission wake-up mode established by the second device to a continuous beacon listening mode in response to not receiving a confirmation from the second device following transmission of the beacon signal.

9. The system of claim 1, wherein the first time period comprises a first portion and a second portion, wherein the first device is configured to provide power from the first power supply to the first communication circuit according to the first communication wake-up mode during the first portion of the first time period and to convert to a third communication wake-up mode during the second portion of the first time period.

10. A method for use in a medical device system comprising a first device comprising a first power supply, a physiological sensor for sensing a signal in a patient, and a first communication circuit, and a second device comprising a second power supply and a second communication circuit configured for bidirectional communication with the first communication circuit, the method comprising:
   setting a first communication wake-up mode for a first time period, that corresponds to a pre-implant time period for the first device, for controlling power provided from the first power supply to the first communication circuit;
   detecting a first event that satisfies a first communication wake-up condition during the first time period and, in response, providing power from the power supply to the first communication circuit and establishing a first communication session between the first device and the second device, wherein the first communication session occurs during the first time period and is enabled according to the first communication wake-up mode;
   during the first communication session, receiving instructions from the second device to establish a second communication wake-up mode for a second time period that corresponds to a post-implant time period for the first device in the patient; and
   detecting a second event that satisfies a second communication wake-up condition during the second time period and, in response, providing power from the power supply to the first communication circuit and establishing a second communication session between the first device and the second device, wherein the second communication session occurs during the second time period and is enabled according to the second communication wake-up mode.

11. The method of claim 10, the first communication wake-up mode comprises one of a manual wake-up mode, an implant detection wake-up mode, and a beacon listening mode.

12. The method of claim 10, wherein the second communication wake-up mode comprises one of a scheduled transmission wake up mode, a continuous beacon listening mode, and a scheduled beacon listening mode.

13. The method of claim 10, wherein the first device comprises a wake-up element for detecting a wake-up condition and the first communication wake-up mode comprises detecting a wake-up condition and enabling a beacon listening mode in response to detecting the wake-up condition.

14. The method of claim 13, further comprising disabling the wake-up element detecting a wake-up condition during the second time period.

15. The method of claim 10, further comprising enabling a manual wake-up element included in the first device during the second time period for generating a wake-up interrupt signal received by a control processor in response to a user intervention and disabling the manual wake-up element during the first time period.

16. The method of claim 10, wherein establishing the second communication wake-up mode comprises establishing a scheduled transmission wake-up mode including a time interval for the scheduled transmission, and transmitting a beacon signal from the first communication circuit to the second device upon expiration of the scheduled transmission time interval.

17. The method of claim 16, further comprising converting the scheduled transmission wake-up mode established by the second device to a continuous beacon listening mode in response to not receiving a confirmation from the second device following transmission of the beacon signal.

18. The method of claim 10, wherein the first time period comprises a first portion and a second portion, wherein the first device provides power from the first power supply to the first communication circuit according to the first communication wake-up mode during the first portion of the first time period and converts to a third communication wake-up mode during the second portion of the first time period.

19. The system of claim 1, wherein the second communication wake-up mode is established by the second device based on a type of the signal.

20. The method of claim 10, wherein the second communication wake-up mode is established by the second device based on a type of the signal.

* * * * *